United States Patent
Tsubouchi

(10) Patent No.: US 7,172,550 B2
(45) Date of Patent: Feb. 6, 2007

(54) ADJUSTABLE COUPLING MECHANISM FOR THE CONDUIT ON A VENTRICULAR ASSIST DEVICE

(75) Inventor: Takeshi Tsubouchi, Ann Arbor, MI (US)

(73) Assignee: Terumo Corporation, Tokyo (JP)

( * ) Notice: Subject to any disclaimer, the term of this patent is extended or adjusted under 35 U.S.C. 154(b) by 131 days.

(21) Appl. No.: 10/630,748

(22) Filed: Jul. 31, 2003

(65) Prior Publication Data

US 2005/0033107 A1     Feb. 10, 2005

(51) Int. Cl.
*A61N 1/362* (2006.01)
(52) U.S. Cl. ......................................... 600/16; 606/153
(58) Field of Classification Search ............ 600/16–18; 623/2, 3, 900; 606/194, 195, 153, 156; 604/8, 604/264, 533, 534, 538
See application file for complete search history.

(56) References Cited

U.S. PATENT DOCUMENTS

| | | | | |
|---|---|---|---|---|
| 2,210,178 A | * | 8/1940 | Recker | ........................ 277/622 |
| 2,305,617 A | * | 12/1942 | Hansell | ........................ 315/374 |
| 2,552,768 A | * | 5/1951 | Brophy | ..................... 285/334.5 |
| 3,168,104 A | * | 2/1965 | Mathis | ................... 137/247.51 |
| 5,498,043 A | * | 3/1996 | Goldenberg | ................. 285/242 |
| 5,810,708 A | * | 9/1998 | Woodard et al. | ............... 600/16 |
| 6,001,056 A | | 12/1999 | Jassawalla et al. | |
| 6,146,325 A | * | 11/2000 | Lewis et al. | ................... 600/16 |
| 6,290,639 B1 | | 9/2001 | Mussivand et al. | |
| 6,346,071 B1 | * | 2/2002 | Mussivand | .................... 600/16 |

* cited by examiner

*Primary Examiner*—Michael J. Hayes
*Assistant Examiner*—Michael G. Mendoza
(74) *Attorney, Agent, or Firm*—Buchanan Ingersoll & Rooney PC

(57) ABSTRACT

A conduit assembly for attachment to a mechanical circulatory device, such as a VAD, and a method of using the same. The conduit assembly includes a conduit having a first rigid, curved conduit and a second rigid, curved conduit. A first coupling attaches a first end of the first rigid, curved conduit to the mechanical circulatory device, the coupling being movable between a rotatable position and a fixed position. The conduit assembly further includes a second coupling for attaching a second end of the first rigid, curved conduit to the second rigid, curved conduit, the second coupling being movable between a rotatable position and a fixed position.

10 Claims, 4 Drawing Sheets

ADJUSTABLE COUPLING MECHANISM FOR THE CONDUIT ON A VENTRICULAR ASSIST DEVICE

TECHNICAL FIELD

The present invention relates to a ventricular assist device (VAD), and more particularly to a system for rotatably adjusting the connection of the inflow and/or outflow conduit on a VAD about two or more axes of rotation.

BACKGROUND OF THE INVENTION

With recent medical developments, the human life expectancy is becoming longer, however, the ratio of cardiac failure to all the various causes of death is also increasing. Mechanical circulatory devices (MCDs) including artificial hearts and ventricular assist devices (VADs) have increased in use due to the corresponding increase in cardiac failure. An artificial heart is used in place of a natural heart. VADs are used when the natural heart is diseased or has been injured by trauma or heart attack, to recover and continue life, either while the natural heart heals, while awaiting a heart transplant, or even on a long-term basis. Hereinafter the present invention is mainly described referring to VADs. However, the invention may be also applied to artificial hearts, other than those aspects respecting to connection with a natural heart.

Left-ventricular assist devices (LVAD) are recognized as potentially very valuable for assisting patients who suffer from congestive heart failure. The LVAD was developed for the treatment of end stage congestive heart failure in patients who are on maximal medical therapy and require long-term mechanical circulatory support, for example, patients who are not (temporarily or permanently) candidates for heart transplantation.

A LVAD is able to assume the function of the left ventricle, and thus continue perfusion of oxygen-rich blood into the body. The LVAD attaches to the patient's natural heart, and to a natural artery, and can be removed if the natural heart recovers. Some LVADs are surgically implanted into the patient's abdominal cavity, while others remain outside the body and are placed in fluid communication with the heart via elongated cannulas. Blood flow in the LVAD is effected by expansion and contraction of a variable-volume chamber. One-way valves associated with the inflow and outflow ports of the LVAD provide for blood flow into the variable-volume chamber during expansion, and for blood flow out of this chamber, usually to the ascending thoracic aorta. A pair of conduits respectively connect the inlet port of the assist device to the left ventricle and the outlet port to the major artery which is to receive the blood flow from the device. A typical LVAD is shown and described in U.S. Pat. No. 6,001,056, the entire contents of which are hereby incorporated by reference.

Alternatively, a VAD can be applied to replace or augment the function of the right ventricle (RVAD). As such, for the purposes of the present invention, the use of VAD applies to both LVADs and RVADs.

With reference to FIG. 1, a patient 10 is shown in fragmentary front elevational view. Surgically implanted into the patient's abdominal cavity 12 is the pumping portion 14 of a ventricular assist device, generally referenced with the numeral 16. The ventricular assist device 16 includes an inflow conduit 18 conveying blood from the patient's left ventricle into the pumping portion 14, and an outflow conduit 20 conveying blood from the pumping portion 14 to the patients ascending thoracic aorta. From the pumping portion 14, a power cable 22 extends outwardly of the patient's body via an incision to a compact controller 24. A power source, such as a battery pack worn on a belt about the patient's waist, and generally referenced with the numeral 26, is connected with the controller 24.

Each of the conduits 18, 20 includes a tubular metallic housing proximate the pumping portion 14 of the device which may connect to elongated flexible segments extending to the heart and ascending aorta, respectively. At the end of the inflow conduit 18 which is connected to the patient's heart, and at the end of the outflow conduit 20 which is connected to the ascending thoracic aorta, the conduits are generally attached to the natural tissue by sutures through the use of an apical sewing ring so that blood flow communication is established and maintained.

The distal end of the inflow conduit 18 is inserted through the ventricle wall and into the heart in order to establish blood flow from the heart to the pumping portion 14. The adjustability of the position of the inflow conduit is important in order to obtain proper orientation and positioning of the VAD. Conventional VADs have included a single rotatable connection within an otherwise rigid inflow conduit. Due to the variation in patient size and chest cavity dimensions, however, it has been found that a single rotatable connection does not provide adequate adjustability for many VAD implantation situations.

Accordingly, there exists a need for greater adjustability of the inflow conduit which extends from the VAD to interior to the ventricular wall of the heart and/or the outflow conduit which conveys blood from the VAD to the ascending thoracic aorta, so as to enable better orientation and positioning of an implantable VAD or other mechanical circulatory device.

SUMMARY OF THE INVENTION

The present invention provides a conduit assembly for attachment to a mechanical circulatory device. The conduit assembly comprises a conduit for conducting blood between a patient and the mechanical circulatory device, the conduit including a first curved conduit and a second curved conduit, a first coupling for attaching a first end of the first curved conduit to the mechanical circulatory device, the coupling being movable between a rotatable position wherein the first curved conduit is rotatable relative to the mechanical circulatory device, and a fixed position wherein the first curved conduit is fixedly positioned relative to the mechanical circulatory device. The conduit assembly further comprises a second coupling for attaching a second end of the first curved conduit to the second curved conduit, the coupling being movable between a rotatable position wherein the first curved conduit is rotatable relative to the second curved conduit, and a fixed position wherein the first curved conduit is fixedly positioned relative to the second curved conduit.

A further aspect of the present invention is directed to a method for implanting a circulatory apparatus in a patient, the apparatus comprising a mechanical circulatory device and a conduit assembly for attachment to the mechanical circulatory device, the conduit assembly including a first conduit and a second conduit. The method comprises the steps of attaching one end of the first conduit to the mechanical circulatory device with a first coupling in a rotatable position, positioning the mechanical circulatory device relative to the patient, rotating the first conduit until a desired position of the first conduit relative to the patient is achieved, and moving the first coupling to a fixed position.

The method further comprises attaching another end of the first conduit to the second conduit with a second coupling in a rotatable position, positioning the mechanical circulatory device relative to the patient, rotating the second conduit until a desired position of the second conduit relative to the patient is achieved, and moving the second coupling to a fixed position.

BRIEF DESCRIPTION OF THE DRAWINGS

For further understanding of the nature and objects of the present invention, references made to the following detailed description taken in conjunction with the accompanying drawings in which like parts are given like reference numerals, wherein.

DETAILED DESCRIPTION OF THE PRESENT INVENTION

Figure 1:
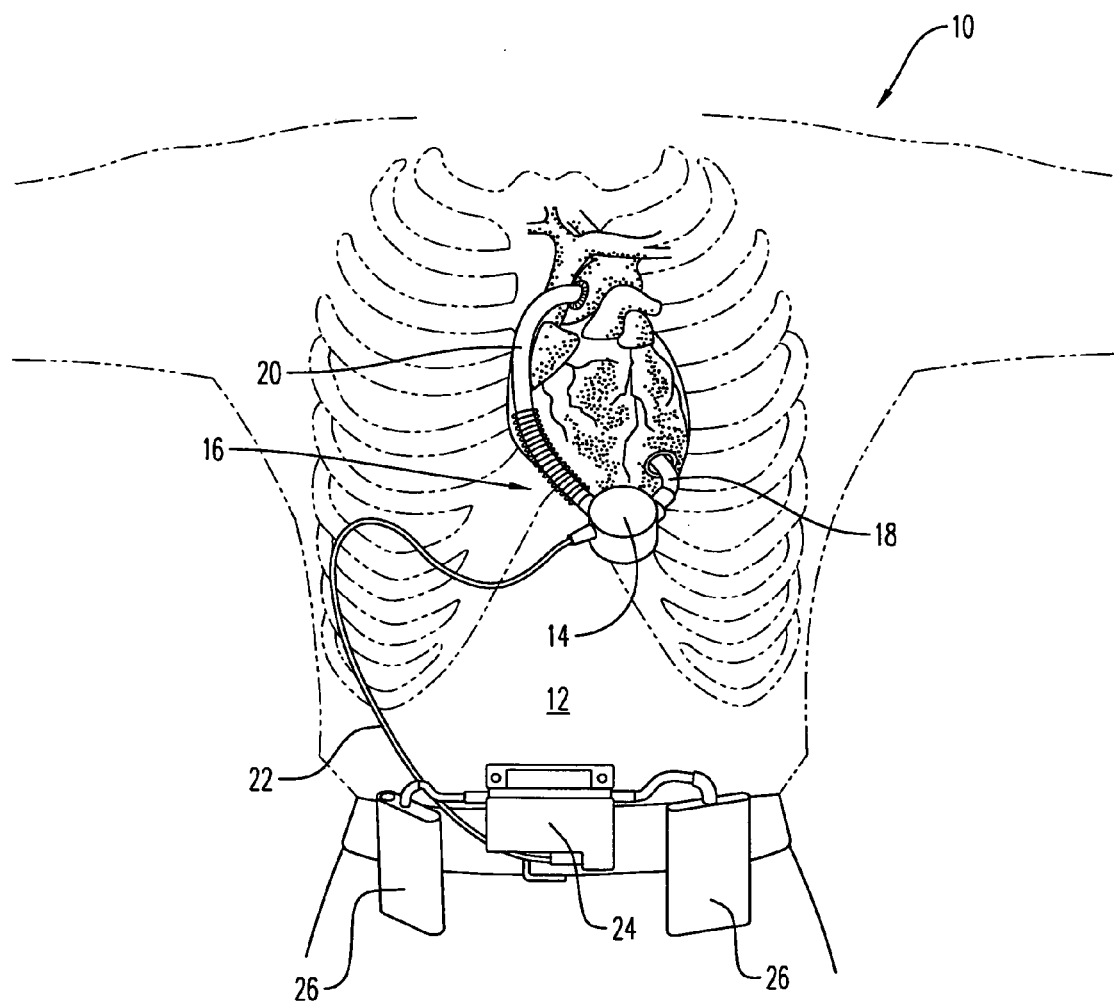
FIG. 1 is a front view of an exemplary ventricular assist device illustrated connected to a heart of a patient.
Figure 2:
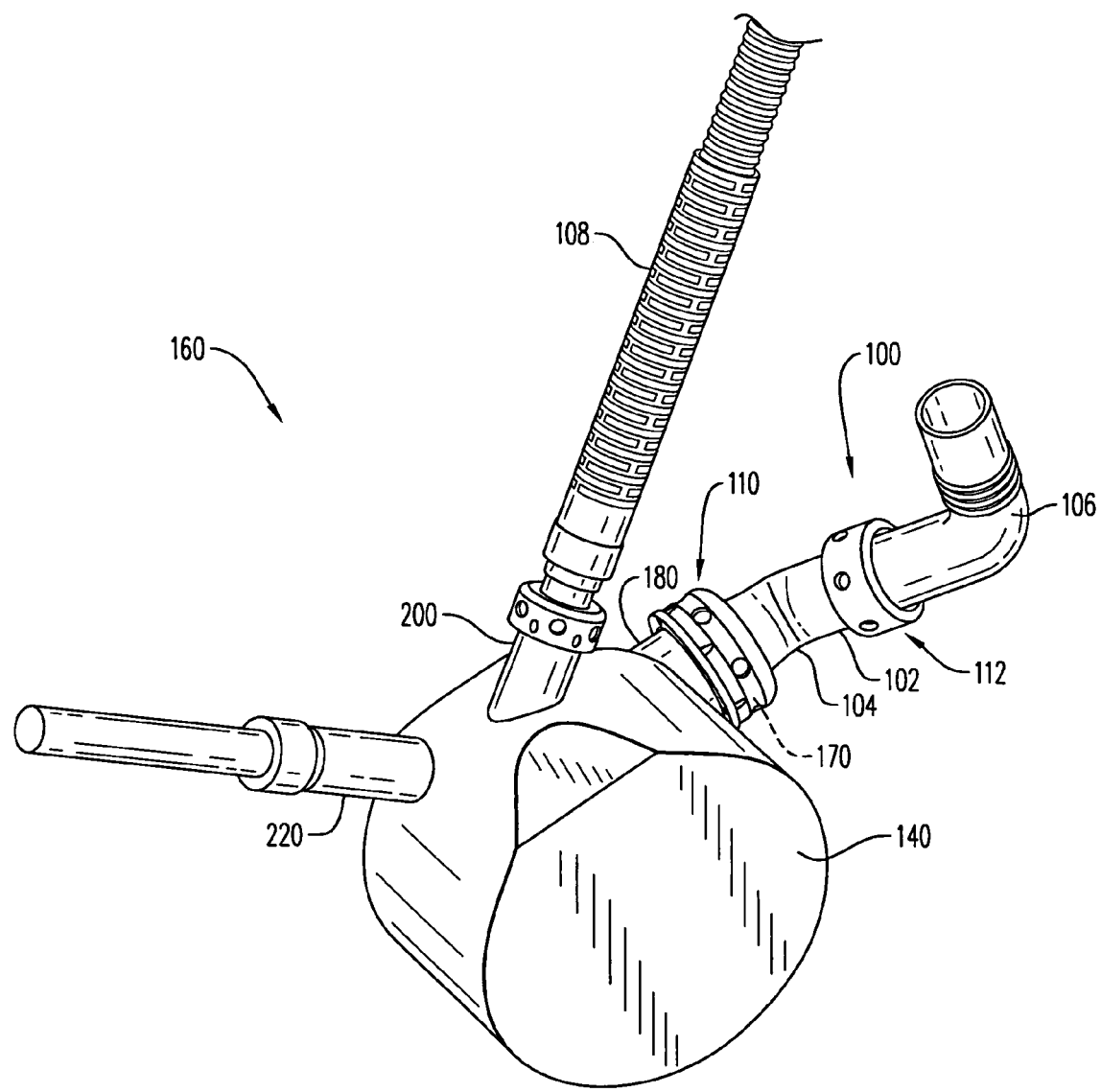
FIG. 2 is a perspective view of a conduit assembly according to the present invention applied to a VAD.

Referring to FIG. 2, the present invention is directed to a conduit assembly, shown generally by reference numeral 100, for a mechanical circulatory device, such as a VAD. In a preferred embodiment, conduit assembly 100 is rigid and preferably made of titanium to provide for strength and durability of the conduit assembly 100. Conduit assembly 100 is preferably utilized as an inflow conduit assembly 102 for insertion into the ventricle of a patient and has a preferred diameter of approximately 14 mm. Other materials and conduit diameters could of course also be used without departing from the scope of the present invention. For instance, plastic materials such as ultra high molecular polyethylene could also be used and larger or smaller diameter conduits could be used depending upon the size of the patient, human or animal, into which the VAD is being implanted.

FIG. 2 shows a VAD 160 to which a preferred embodiment of the conduit assembly 100 of the present invention is suitably attached. The VAD 160 has a pumping portion 140 having an inflow port 180, an outflow port 200, and a connection 220 for attachment of a power cable. At the inflow port 180, an inflow conduit assembly 102 is provided to connect the pumping portion 140 to the natural heart of a patient. At the outflow port 200, an outflow conduit assembly 108 is provided to connect the pumping portion to the thoracic aorta of the patient. The outflow conduit assembly 108 may also be connected to a different part of the blood circulation system.

In operation, blood is pumped from the heart into the pumping portion 140 of VAD 160 through the inflow conduit assembly 102. The VAD 160 then pumps the blood out of the pumping portion 140 into the thoracic aorta through the outflow conduit assembly 108.

The inflow conduit assembly 102 preferably comprises one or more conduits or tubes, such as proximal tube 104 and distal tube 106 as shown in FIG. 2. The proximal tube 104 is preferably curved or angled to minimize interference with adjacent organs. The shape of the proximal tube 104 is dictated by the desire of minimizing interference with adjacent organs and thus may include only one bend at any predetermined angle, such as the illustrated elbow tube, or form other shapes such as an S-shaped conduit. In order to connect such a curved rigid tube 104, the conduit assembly 102 uses a proximal coupling 110 which is movable between a rotatable position and a fixed position. In the rotatable position, the proximal tube 104 is free to rotate about its longitudinal axis relative to the VAD 160 so that it can be positioned at a desired angle to avoid interference with adjacent organs. The axis of the proximal tube 104 curves as the tube 104 curves. The tube 104 rotates about its longitudinal axis at the tube section engaging the port on the VAD 160. The VAD 160 may have one or more extension tubes at the respective port, and in that instance, the tube 104 rotates about the axis of the tube section engaging with the nearest extension tube. After the angle of the proximal tube 104 is decided, the proximal coupling 110 is rotatably moved to the fixed position so that the proximal tube 104 is immovably positioned relative to the VAD 160, as explained in greater detail below.

The distal tube 106 is also preferably curved or angled to minimize interference with adjacent organs and may similarly have one or more bends at any predetermined angle. In order to connect such a curved rigid tube 106 to the curved rigid tube 104, the conduit assembly 102 also preferably includes a distal coupling 112 which is movable between a rotatable position and a fixed position. In the rotatable position, the distal tube 106 can be rotated about its longitudinal axis relative to the proximal tube 104 so that it can be positioned at a desired angle to avoid interference with adjacent organs. The axis of the distal tube 106 curves as the tube 106 curves. The tube 106 rotates about its axis at the tube section engaging with the proximal tube 104. After the angle of the distal tube 106 is decided, the coupling 112 is rotatably moved to the fixed position so that the distal tube 106 is immovably positioned relative to the proximal tube 104, as explained in greater detail below.

Figure 3:
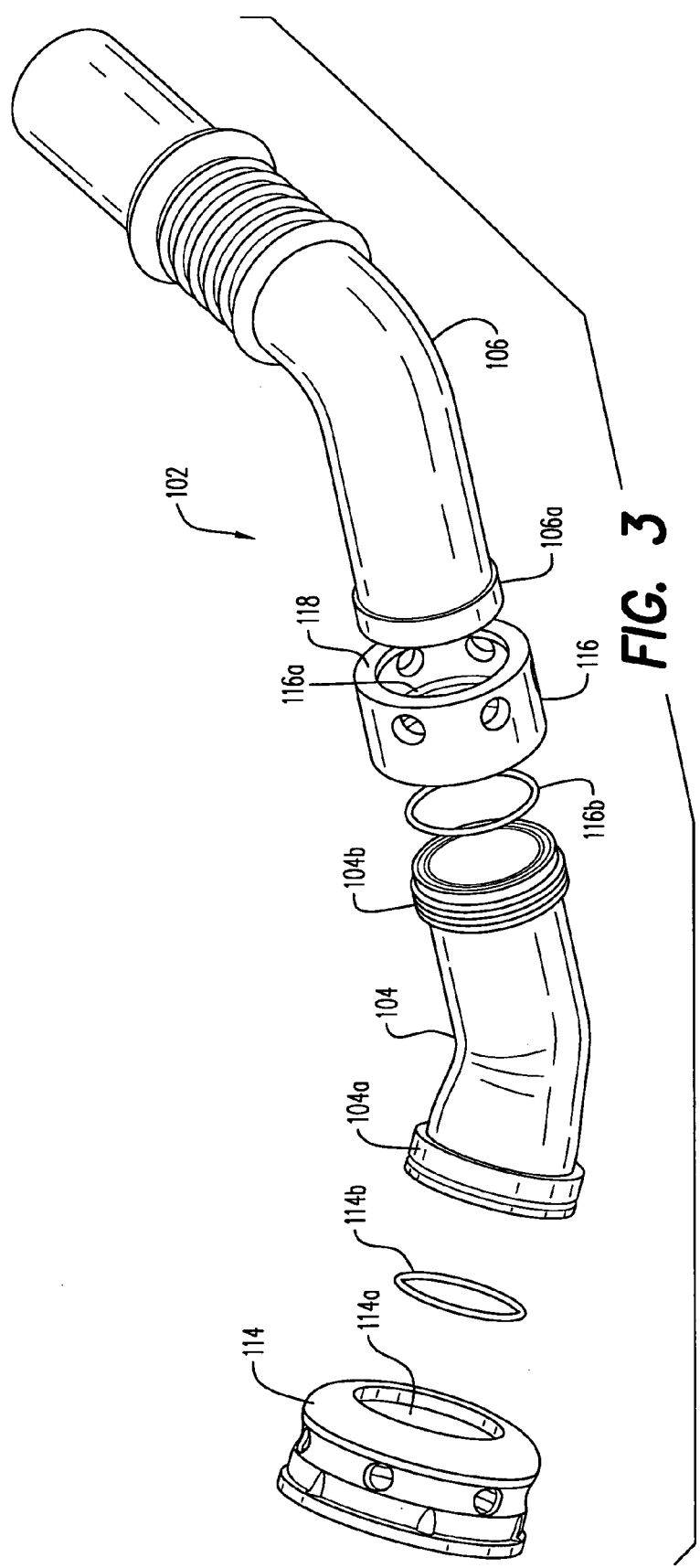
FIG. 3 is an exploded view of the conduit assembly shown in FIG. 2.
Figure 4:
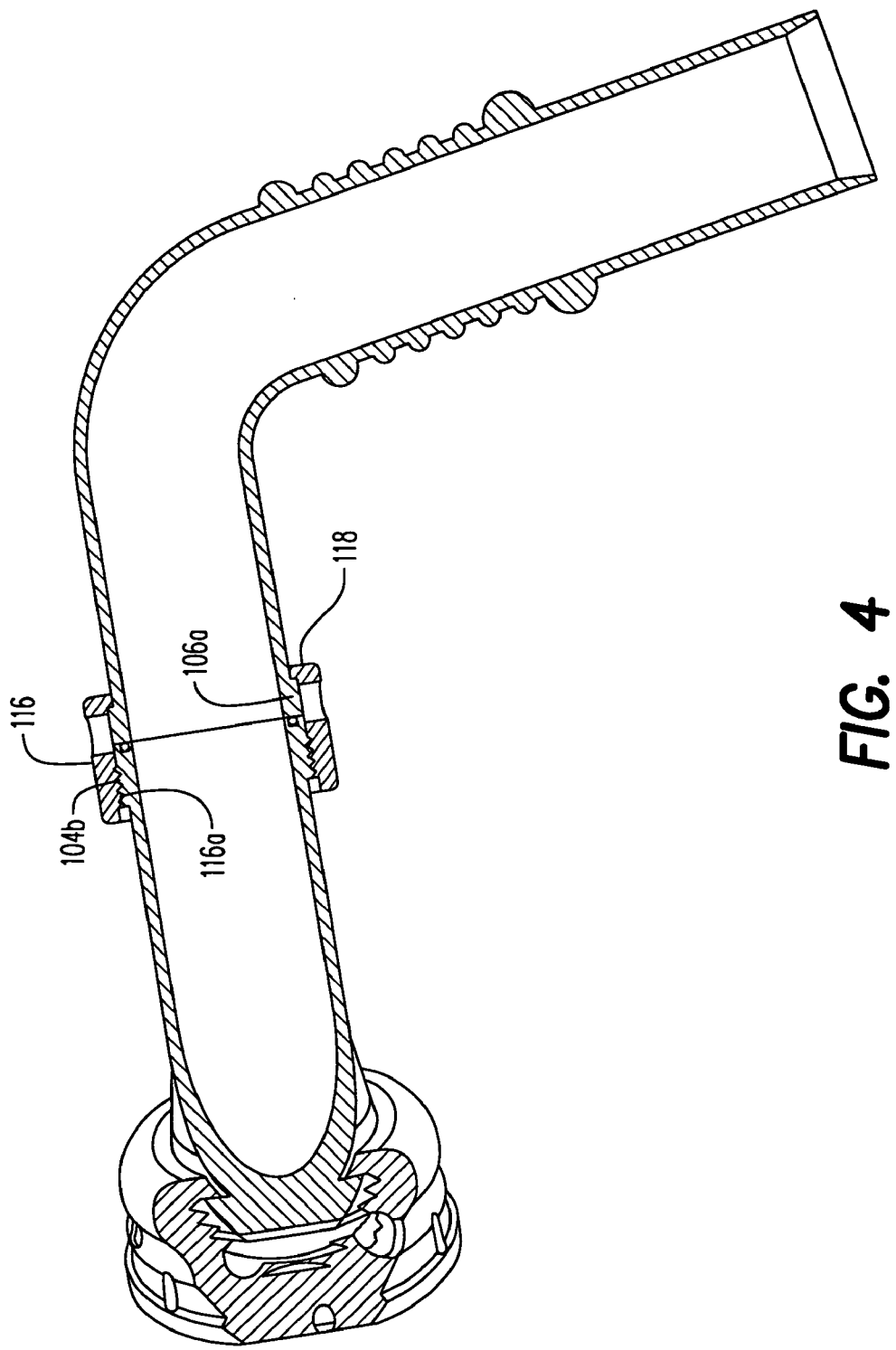
FIG. 4 is a cross-sectional view taken generally along the central axis of the distal conduit shown in FIG. 2.

FIG. 3 shows an exploded view of the inflow conduit assembly 102 in accordance with a preferred embodiment of the invention. As more clearly shown, the proximal tube or conduit 104 includes threaded ends 104a, 104b to which proximal coupling 110 is secured at one end and to which distal coupling 112 is secured at the other end. Proximal coupling 110 preferably comprises a rotatable nut 114 including a female threaded coupling 114a for receiving threaded end 104a of proximal conduit 104, with a gasket 114b preferably disposed therebetween. The rotatable nut 114 is also attached to a corresponding male threaded connector 170 extending from the inflow port 180 of the VAD. Distal coupling 112 preferably comprises rotatable nut 116 including a female threaded coupling 116a for receiving threaded end 104b of proximal conduit 104, with a gasket 116b preferably disposed therebetween. Rotatable nut 116 also preferably includes a lip 118 for engaging the flange 106a on the proximal end of distal tube 106, as shown most clearly in FIG. 4.

The nuts 114, 116 provide a rotatable joining of the proximal tube 104 and the distal tube 106 during the implantation of the VAD. More specifically, the nuts 114, 116 move between a rotatable position and a fixed or locked position. When in the rotatable position, the nut 114 allows the proximal conduit 104 to rotate about its axis into any rotated position relative to inflow port 180 of VAD 160, when the VAD is implanted. This allows flexibility in positioning of the inflow conduit assembly 102. This positioning flexibility is advantageous, considering the difference in anatomies from patient to patient. During the fitting of the VAD, an optimal position for the proximal conduit 104 is determined. Then, the proximal conduit 104 is fixed or locked in the desired optimal position by rotating or otherwise tightening the rotatable nut 114 to the fixed position.

When in the rotatable position, the nut 116 allows the distal conduit 106 to rotate about its axis into any rotated position relative to proximal conduit 104, when the VAD is implanted. This allows further flexibility in positioning of the inflow conduit assembly 102 due to the adjustability of the position and orientation of the VAD about two independent axes. This improved positioning flexibility is extremely advantageous considering the differences in patient size. During the fitting of the VAD, after an optimal position for the distal conduit 106 is determined, the distal conduit 106 is fixed or locked in the desired optimal position by rotating or otherwise tightening the rotatable nut 116 to the fixed position.

Although the above detailed description of positioning or fitting the VAD describes first fixing the position of the proximal tube 104 relative to the VAD 160 and thereafter fixing the position of the distal tube 106 relative to the proximal tube 104, one skilled in the art will appreciate that the order of fixing the couplings 110 and 112 is discretionary with the surgeon and will depend upon many factors, and may in fact be done substantially simultaneously.

Further, while the preferred embodiment described above refers to an inflow conduit assembly having a proximal portion with lockable couplings at each end for connection to the inflow port and a distal conduit, respectively, one skilled in the art should appreciate that the same principles of increased flexibility in positioning the VAD are equally applicable to the outflow conduit assembly 108. Accordingly, it is within the scope of the present invention to provide such a conduit assembly for the inflow and/or outflow of a VAD or other mechanical circulatory device.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

What is claimed is:

1. A method for implanting a circulatory apparatus in a patient, the apparatus comprising a mechanical circulatory device and a conduit assembly for attachment to the mechanical circulatory device, the conduit assembly including a first rigid curved conduit and a second rigid curved conduit; the method comprising the steps of:
   attaching one end of the first rigid curved conduit to the mechanical circulatory device with a first coupling in a rotatable position;
   positioning the mechanical circulatory device relative to the patient;
   rotating the first rigid curved conduit until a desired position of the first conduit relative to the patient is achieved;
   moving the first coupling to a fixed position so as to maintain a predetermined orientation of the first rigid curved conduit when the first coupling is disposed in the fixed position;
   attaching another end of the first rigid curved conduit to the second rigid curved conduit with a second coupling in a rotatable position;
   positioning the mechanical circulatory device relative to the patient;
   rotating the second rigid curved conduit until a desired position of the second rigid curved conduit relative to the patient is achieved; and
   moving the second coupling to a fixed position so as to maintain a predetermined orientation of the second rigid curved conduit when the second coupling is disposed in the fixed position;
   wherein the first rigid curved conduit and the second rigid curved conduit provide increased adjustability in positioning the circulatory apparatus relative to the patient.

2. A method for implanting a circulatory apparatus according to claim 1, wherein the first rigid curved conduit and the second rigid curved conduit are circular in cross-section.

3. A method for implanting a circulatory apparatus according to claim 1, wherein the first rigid curved conduit and the second rigid curved conduit are formed from titanium.

4. A method for implanting a circulatory apparatus according to claim 1, wherein the first coupling comprises a first rotatable nut, the first rotatable nut being movable between a rotatable position wherein the first rigid conduit is rotatable relative to the mechanical circulatory device, and a fixed position wherein the first rigid curved conduit is fixed relative to the mechanical circulatory device.

5. A method for implanting a circulatory apparatus according to claim 4, wherein the first rotatable nut engages a correspondingly threaded inflow port on the mechanical circulatory device.

6. A method for implanting a circulatory apparatus according to claim 4, wherein the second coupling comprises a second rotatable nut, the second rotatable nut being movable between a rotatable position wherein the second rigid curved conduit is rotatable relative to the first rigid curved conduit, and a fixed position wherein the second rigid curved conduit is fixed relative to the first rigid curved conduit.

7. A method for implanting a circulatory apparatus according to claim 6, wherein the second rotatable nut engages the second end of the first rigid curved conduit, the second end of the first rigid curved conduit being correspondingly threaded.

8. A method for implanting a circulatory apparatus according to claim 7, wherein the second rotatable nut includes a lip for engaging the first end of the second rigid curved conduit, the first end of the second rigid curved conduit including a flange.

9. A method for implanting a circulatory apparatus according to claim 1, wherein the conduit defines a conduit for conducting blood between a patient and a ventricular assist device.

10. A method for implanting a circulatory apparatus according to claim 9, wherein said conduit defines a conduit for conducting blood between a patient and a left ventricular assist device.

* * * * *